(12) United States Patent
Nikou et al.

(10) Patent No.: US 11,471,169 B1
(45) Date of Patent: Oct. 18, 2022

(54) TRACKED SURGICAL TOOL WITH FLEXIBLE LUMEN AND EXPOSURE CONTROL

(71) Applicant: Smith & Nephew, Inc., Memphis, TN (US)

(72) Inventors: Constantinos Nikou, Monroeville, PA (US); Christoph Kolja Boese, Hamburg (DE)

(73) Assignee: Smith & Nephew, Inc., Memphis, TN (US)

( * ) Notice: Subject to any disclaimer, the term of this patent is extended or adjusted under 35 U.S.C. 154(b) by 452 days.

(21) Appl. No.: 16/733,910

(22) Filed: Jan. 3, 2020

Related U.S. Application Data

(63) Continuation of application No. 16/240,888, filed on Jan. 7, 2019, now abandoned.

(51) Int. Cl.
| | |
|---|---|
| A61B 17/16 | (2006.01) |
| A61B 34/30 | (2016.01) |
| A61B 34/20 | (2016.01) |
| A61B 17/32 | (2006.01) |
| A61B 34/00 | (2016.01) |
| A61B 17/00 | (2006.01) |

(52) U.S. Cl.
CPC .... *A61B 17/1628* (2013.01); *A61B 17/32002* (2013.01); *A61B 34/20* (2016.02); *A61B 34/30* (2016.02); *A61B 34/71* (2016.02); *A61B 34/74* (2016.02); *A61B 17/1631* (2013.01); *A61B 17/1668* (2013.01); *A61B 2017/00318* (2013.01); *A61B 2034/2051* (2016.02); *A61B 2034/2055* (2016.02); *A61B 2034/2068* (2016.02); *A61B 2034/301* (2016.02); *A61B 2034/305* (2016.02); *A61B 2034/715* (2016.02); *A61B 2034/743* (2016.02)

(58) Field of Classification Search
CPC .......... A61B 17/1628; A61B 17/32002; A61B 34/20; A61B 34/30; A61B 34/71
USPC .................................. 318/560; 606/79, 53, 1
See application file for complete search history.

(56) References Cited

U.S. PATENT DOCUMENTS

| | | | |
|---|---|---|---|
| 5,290,303 | A | 3/1994 | Pingleton et al. |
| 5,520,634 | A * | 5/1996 | Fox .................. A61B 17/32002 606/180 |
| 7,914,464 | B2 | 3/2011 | Burdorff et al. |
| 8,894,654 | B2 | 11/2014 | Anderson |
| 8,961,536 | B2 | 2/2015 | Nikou et al. |
| 2009/0118742 | A1 | 5/2009 | Hartmann et al. |
| 2011/0245833 | A1 | 10/2011 | Anderson |
| 2011/0264107 | A1 | 10/2011 | Nikou et al. |

(Continued)

FOREIGN PATENT DOCUMENTS

| | | |
|---|---|---|
| WO | 2011021192 A1 | 2/2011 |
| WO | 2018132835 A1 | 7/2018 |

*Primary Examiner* — David Luo
(74) *Attorney, Agent, or Firm* — DLA Piper LLP

(57) ABSTRACT

A tool for surgically removing tissue of a patient includes a body, a flexible rotating shaft that drives a distal cutting tool and is drivingly coupled to a motor supported by bearings in a flexible tubular sheath to allow the shaft to rotate and be shifted longitudinally. Steering cables in the sheath control the flexion of the sheath. A processor controls the operation to ensure that the cutting tool operates within a predetermined resection area, controlling a combination of motor speed, sheath flexion, and shaft retraction to assist surgery in the resection area.

19 Claims, 7 Drawing Sheets

(56) References Cited

U.S. PATENT DOCUMENTS

| | | |
|---|---|---|
| 2012/0123418 A1 | 5/2012 | Giurgi et al. |
| 2013/0060278 A1 | 3/2013 | Bozung et al. |
| 2016/0354162 A1 | 12/2016 | Yen et al. |

\* cited by examiner

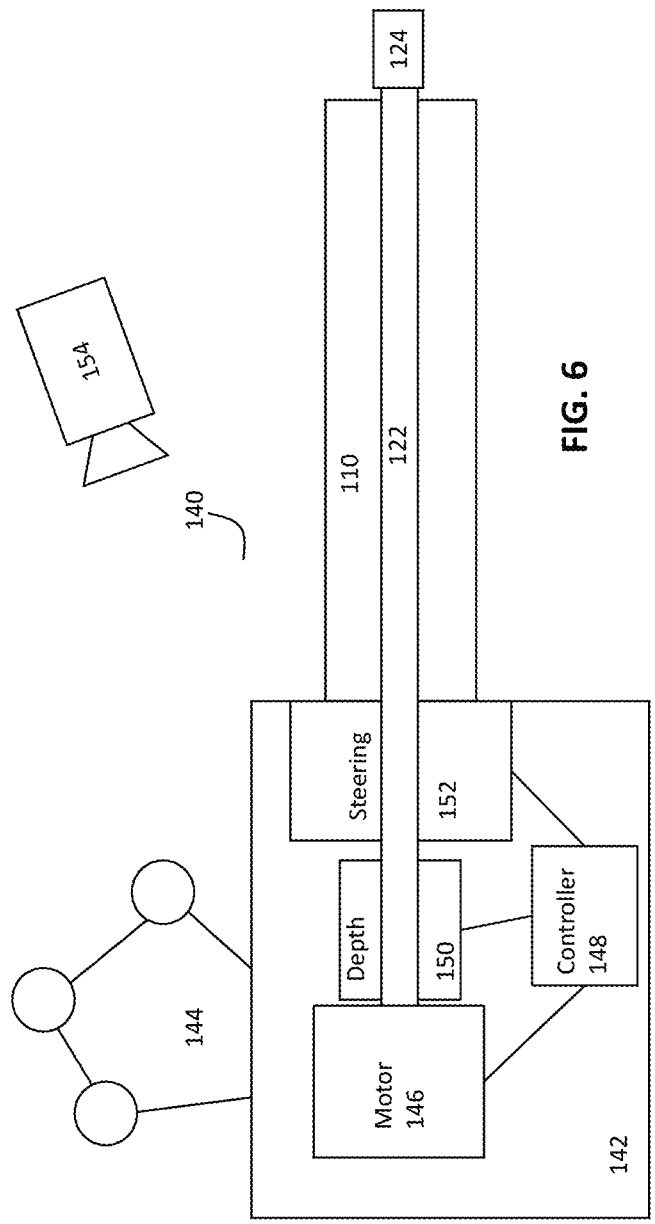

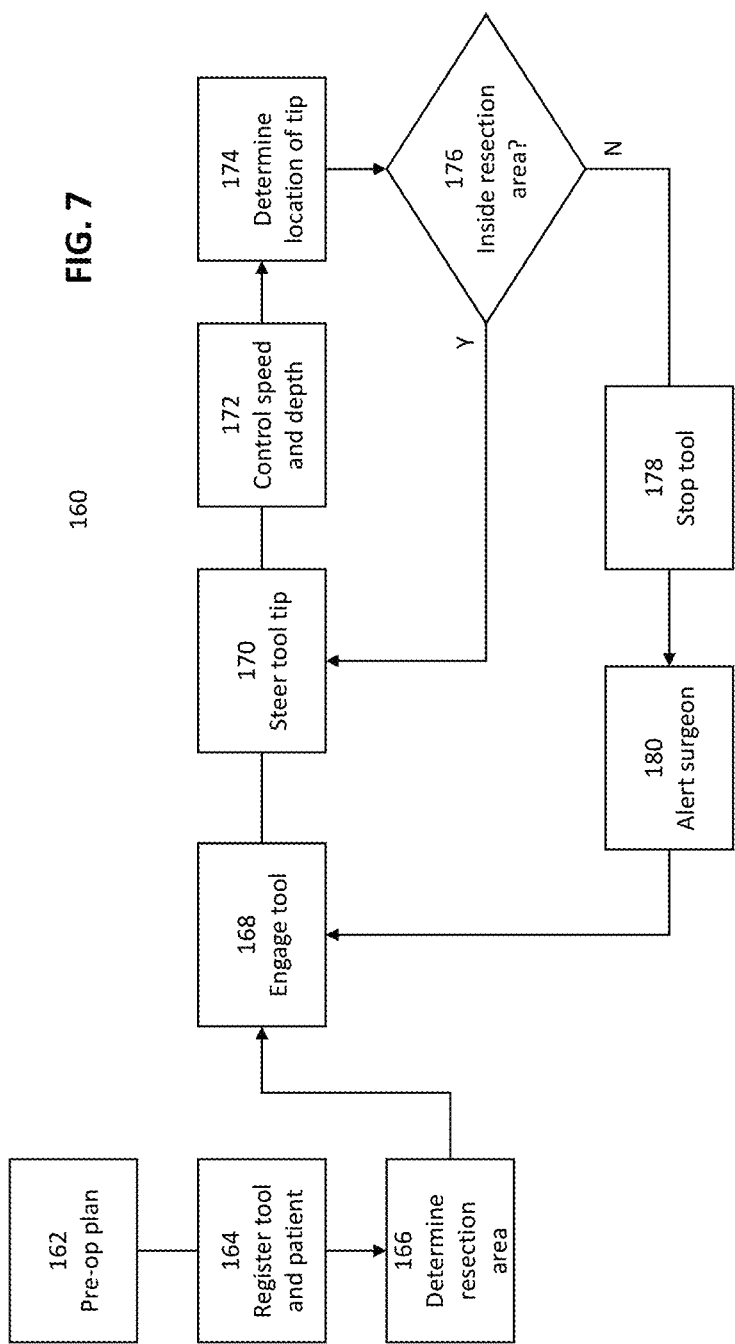

TRACKED SURGICAL TOOL WITH FLEXIBLE LUMEN AND EXPOSURE CONTROL

CROSS-REFERENCE TO RELATED APPLICATIONS

This application is a continuation of U.S. patent application Ser. No. 16/240,888, filed Jan. 7, 2019, entitled "Tracked Surgical Tool with Flexible Lumen and Exposure Control," which is incorporated herein by reference in its entirety.

TECHNOLOGY FIELD

The present invention relates, in general, to a surgical tool and system and use thereof in removing patient tissue and, more particularly, to systems and methods for removing patient tissue using a rotary tool having a controllable flexion.

BACKGROUND

In various surgical procedures, access to and visibility of the tissue being operated upon presents challenges. For example, in curettage of cancerous tissue, particularly in bones, benign tumors and tumor-like lesions can be difficult to find and access manually because the treatment attempts to leave the surrounding bone structure intact. Tumors and other tissues suitable for curettage can include anuerysmatic bone cysts, juvenile bone cysts, giant cell tumors, osteoid-osteoma, and AVN. With traditional curettage, it can be difficult to achieve complete removal of pathologic tissue using straight or rigid instruments. FIG. 1A shows a cross-section of an exemplary femur bone 100 having a tumor 102 within the bone that needs to be surgically removed. To accomplish this, a surgeon will typically drill a hole in the outside of the femur, allowing a curette tool to be inserted into the bone to scrape and scoop out the tumor portion of the bone (or use rotary or other power tools). As shown in FIG. 1B, removal of the entire tumor via a hole that is smaller than the maximum diameter of the tumor can be incomplete using a straight or rigid curette tool to manually resect the tissue. This is because of the angular restriction placed on the tool by the surgeon's hand and the hole. It is generally desirable to utilize the smallest diameter hole possible to fully remove the tumorous tissue. Incomplete removal of tumor tissue is linked to recurrence, putting the patient at risk for multiple surgical interventions and relapse of cancerous symptoms.

In some surgical fields, flexible instruments can be used to perform procedures on bodily tissues. For example, pulmonary and cardiac procedures often use robotically-controlled catheters that can achieve a high degree of flexion, allowing the instrument to travel within vascular walls. These tools include a flexible tubular sheath that includes radially integrated cabling. By applying selective tension and/or extension of the wires in the sheath, the curvature of the flexible sheath can be adjusted by a robot or by the surgeon during the procedure. This can allow a flexible tool to navigate the user's body and to deliver a tooltip at a desired location.

Flexible tools have been proposed in the osteopathic curettage/resection space, such as WO 2017/204869 to Ding, et al. Ding describes the basic mechanical components for a rotary bone-drilling tool with a controllably flexible shaft to direct the rotary tool.

SUMMARY

Embodiments provide a flexible lumen that guides an internal draft to guide a tool during surgery. For example, in some embodiments, a system for surgically removing tissue of a patient includes a tool body containing a motor, a flexible rotating shaft drivingly coupled to the motor, and a flexible tubular sheath located around the flexible rotating shaft, mechanically coupled to the tool body. A plurality of bearings are placed along a lumen of the flexible sheath, providing support to the flexible rotating shaft, and are configured to allow the shaft to rotate and to move longitudinally relative to the sheath. A plurality of steering wires are coupled to the flexible tubular sheath and are configured to control the flexion of the flexible tubular sheath. A cutting tool is placed at a distal end of the flexible rotating shaft. A controller is configured to determine a location of the cutting tool relative to patient tissue and to control the speed of the motor and the longitudinal extension of the flexible rotating shaft in response to the location.

According to aspects of some embodiments, the flexible tubular sheath includes a plurality of slots through a wall of the sheath. In some embodiments, the plurality of bearings include a plurality of bushings. In some embodiments, the tool body is configured to be held by a surgeon, while in some, tool body is configured to be held by robotic end effectors.

According to aspects of some embodiments, the controller is configured to determine whether the cutting tool remains inside a predetermined resection area in the patient tissue. The controller can be configured to retract the cutting tool within the flexible tubular sheath if the cutting tip is determined to be outside of the predetermined resection area. The controller can be configured to control the flexion of the flexible tubular sheath and the longitudinal extension of the flexible rotating shaft based on the position of the tool body, to remove substantially all of the patient tissue within the predetermined resection area. In some embodiments, the controller is configured to control the longitudinal depth of the cutting tool relative to the flexible tubular sheath to compensate for motion of the tool body.

Some embodiments include a camera tracking system that assists the controller in determining the location of the cutting tool, based on the position and orientation of fiducial marks coupled to the tool body.

According to another exemplary embodiment, a system for surgically removing tissue of a patient includes an optical tracking system, having at least one camera, and a tool, having a tool body having fiducial marks to facilitate position and orientation capture by the optical tracking system and containing a motor, a flexible rotating shaft drivingly coupled to the motor, a flexible tubular sheath located around the flexible rotating shaft mechanically coupled at a proximal end to the tool body, a plurality of bearings placed along a lumen of the flexible sheath that support to the flexible rotating shaft. The tool includes a plurality of steering wires coupled to the flexible tubular sheath, configured to control the flexion of the flexible tubular sheath and operatively coupled to a driver to provide tension or extension forces to the plurality of steering wires. A cutting tool is placed at a distal end of the flexible rotating shaft, while the plurality of bearings are configured to allow the shaft to rotate and to move longitudinally relative to the sheath, allowing the cutting tool to rotate and extend and retract relative to the sheath. A controller is configured to determine a location of the cutting tool relative to patient tissue and to control the speed of the motor and the longitudinal extension of the flexible rotating shaft within the flexible tubular sheath in response to the determined location.

In some variations of this embodiment, the controller is configured to determine whether the cutting tool remains inside a predetermined resection area in the patient tissue. In some further variations, the controller is configured to retract the cutting tool within the flexible tubular sheath if the cutting tip is determined to be outside of the predetermined resection area. In some embodiments, the controller is configured to control the flexion of the flexible tubular sheath and the longitudinal extension of the flexible rotating shaft based on the position and orientation of the tool body to remove substantially all of the patient tissue within the predetermined resection area.

According to another embodiment, a method for surgically removing tissue of a patient, includes engaging patient tissue with a rotary cutting tool having a cutting tip on the distal end of a flexible rotating shaft supported in a flexible tubular sheath and a tool body at the proximal end of the sheath having a motor coupled to the shaft, and tracking the position and orientation of the tool body relative to the patient. Additional steps include controlling the flexion of the flexible tubular sheath with one or more steering wires, determining a location of the cutting tip relative to a predetermined resection area in the patient tissue, and adjusting the flexion of the flexible tubular sheath and a longitudinal extension of the flexible rotating shaft in the sheath, under processor control, to remove patient tissue within the predetermined resection area.

According to some variations of this embodiment, the method includes adjusting the extension to compensate for motion of the tool body. The method can also include halting the motor and retracting the cutting tip within the flexible tubular sheath if the cutting tip exceeds the predetermined resection area. Further, the tracking step can include optically tracking fiducial marks on the tool body relative to fiducial marks on the patient.

Additional features and advantages of the invention will be made apparent from the following detailed description of illustrative embodiments that proceeds with reference to the accompanying drawings.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawing:

FIG. 6 is a system diagram of an exemplary rotary tool in accordance with some embodiments;

FIG. 7 is a flow chart of a method for operating a rotary tool in accordance with some embodiments.

DETAILED DESCRIPTION

Figure 1B:
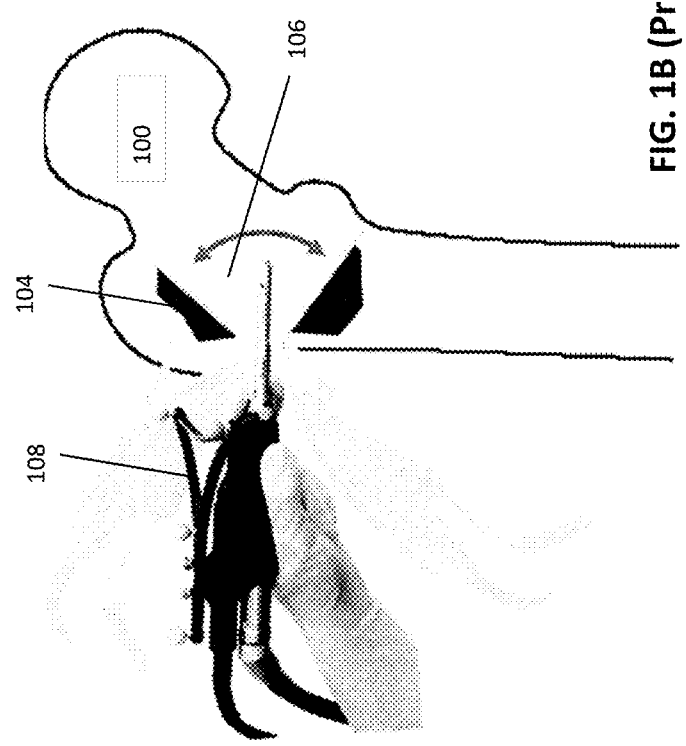
FIG. 1B is a cross-sectional diagrammatic view of the femoral head having tumorous tissue being incompletely removed in the prior art.
Figure 1A:
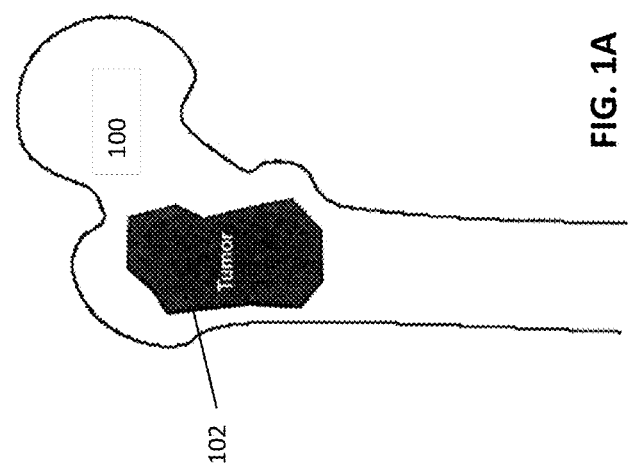
FIG. 1A is a cross-sectional diagrammatic view of the femoral head having tumorous tissue to be removed.

Embodiments of the present invention include a powered surgical tool with a controlled, flexible tubular sheath member and a tooltip/cutting tip/burr coupled to a flexible inner shaft for less-invasive surgical procedures. Bearings or bushings between the lumen of the sheath and the shaft allow the shaft to rotate relative to the lumen and to be extended or retracted longitudinally. In some embodiments, the powered surgical tool is a precision bone removal device, such as the NAVIO® handpiece, which includes a burring device (NAVIO is a registered trademark of BLUE BELT TECHNOLOGIES, INC. of Pittsburgh, Pa. which is a subsidiary of SMITH & NEPHEW, INC. of Memphis, Tenn.). Embodiments can utilize position-sensing instrumentation to allow reliable positional guidance of the tooltip within patient tissue, such as a bone cavity. These sensors allow feedback to users or to a controller about the location of the tooltip. This can be used by a surgeon or a robotic system that controls the operation or location of the tooltip to alter behavior of the tool accordingly.

By providing a flexible tool that includes position-sensing to accurately approximate the location of the tooltip, additional levels of control of that tool and safety features can be utilized. For example, in some embodiments, the ability of the system to independently control the position of a cutting tool relative to the tool body/handpiece allows the tool to be restricted so that it does not leave the intended zone of resection (e.g., a predetermined area within the tissue that should be resected to remove undesirable tissue according to a pre-operative plan). In some embodiments, by knowing the position of the tooltip, the tooltip can be disengaged dynamically such that the tool does not do resect tissue outside the zone of resection. In some embodiments, this can be through stopping or reducing the speed of a rotating tooltip and/or by retracting the tooltip into the sheath to prevent it from engaging tissue outside of the zone of resection when the tooltip is at risk of going outside the predetermined resection area.

Some embodiments include a robotically controlled burr on a flexible shaft within the lumen of a flexible tubular sheath. This can be part of the handpiece that is controlled by a surgeon's hand or as part of a robotically-controlled end effector, where a robot arm controls not only the activation of the tool, but the specific location and flexion of the tool. This can be especially helpful in surgical procedures that seek to use the least invasive means possible for removing tissue.

In some embodiments, a surgical burr is used as a tooltip for a handpiece that is tracked optically, such as the NAVIO handpiece. The burr is a rotary cutting tip with grinding features (such as an abrasive tip or sharpened knurls) that is coupled to a motor via a flexible shaft. The flexible shaft is encased in a lumen of a flexible tubular sheath. That sheath is sufficiently rigid to resist deflection from external forces (e.g., bone impaction as the tool is moved) while having a controllable flexion through the use of integrated wires spaced circumferentially within the rigid, longitudinally expansive/contractive walls of the sheath. Flexion of the tubular sheath guides the flexible shaft, setting the flexion angle of the flexible shaft to locate the surgical burr tip at a specific location within the patient's body. The specific location of the tooltip can be determined given the position and orientation of a controlled handpiece/tool body and the specific flexion (direction and amount) of the shaft or sheath. For example, a surgeon can hold a handpiece with a flexible shaft and insert the burr tip into a hole in a bone and, by changing the position and orientation of the handpiece in his hand, as well as the flexion (both degree and direction) of the flexible sheath, the surgeon (or a robot) can repeatedly and reliably place the tooltip at a specific location in the patient's body. Similarly, once the flexion of the tool is set, the surgeon can change the position or orientation of the handpiece/housing to change the location of the tooltip. Furthermore, based on knowledge of the flexion of the sheath, the characteristics of the tool, and the position and orientation of the handpiece relative to the patient's body, a processor that receives input about the surgical procedure can accurately determine an approximation of the specific position of the tooltip within the patient's body and where the tooltip is relative to a predetermined resection area.

An exemplary flexible tubular sheath includes a sheath having a uniform wall thickness that is placed concentrically around a rotary shaft. Partial circumferential slots are placed in the wall of the sheath, each slot going partially around the circumference of the tubular body of the sheath. By staggering the position of these slots, flexion in any direction can be achieved. For example, if a lumen were designed to only flex in one direction, the partially circumferential slots could be spaced such that each slot goes approximately halfway around the circumference and alternating or adjacent slots are spaced 180° around the circumference of the lumen. This makes flexion in the plane defined by the centers of those slots feasible. If slots are spaced such that they intersect the wall of the lumen regularly along any longitudinal path on the surface of the sheath, flexion in a radial plane defined by the center of the tube and that longitudinal path is achievable.

Slots can be any suitable shape, as determined by a person of ordinary skill in the art, including holes that are elongated circumferentially and have generally parallel sides in the longitudinal direction. The exact size and length of these slots can vary depending on the desired properties and the size of the tubular member. In some embodiments, an exemplar member has a substantially uniform wall thickness chosen from the range of 0.25-5 mm+/−5%, depending on the desired mechanical properties. In some embodiments, slots can be on that same size order. Note that the spacing and size of slots relative to wall thickness can determine maximum flexion and the mechanical forces needed to cause flexion (for a given material and diameter)—larger and more frequent slots allow more and easier flexion. Meanwhile, thicker walls, more rigid materials, and a larger tube diameter can make it harder to flex the tubular member. In some embodiments, slots are aligned such that within a given longitudinal distance, there are one, two, or three slots along that circumference (the exact number being chosen to cause the rigidity/flexibility properties desired). Slot groups adjacent longitudinally are preferably offset by a predetermined angle to form a helical (or double helical) pattern of slots along the length of the tube for uniform flexibility. The ratio along the circumference of slots to solid material can be chosen to meet the desired flexibility criteria (for example, 100 degree slots and 80 degree solid portions for two slots at a given longitudinal location). Slots can have non-rectangular shapes in some embodiments, taking on rounded or enlarged ends (e.g., for durability) or more ovoid shapes (e.g., to increase flexibility in a subset of directions). In some embodiments, the parallel circumferential walls of the slots are approximately perpendicular to the outer surface of the sheath, while the ends are whatever shape makes manufacturing practical, such as ramped when the slots are cut using a disc-shaped saw blade.

The material choice for the flexible tubular sheath can be any suitable rigid material that can be sterilized for use in surgical procedures and has suitable deformation properties to allow controlled flexion. Exemplary materials include stainless spring steel, titanium, nitinol, or rigid polymers that resist deformation over time. The exact choice of material, dimensions, wall thickness, and slot geometry, as well as the desired rigidity and flexibility of the sheath structure can be selected by a person of ordinary skill for a given application.

To achieve controlled flexion of the tube, a plurality of wires are placed in passages in the walls of the tube, allowing the wires to slide relative to any portion of the wall of the tube. In some embodiments, the tubular sheath includes tubes within the walls that are sized to allow a metal steering wire to be embedded, and slide relative to the tubular structure of the sheath. Preferably, the passages for guiding the steering wires are drilled longitudinally into the tubular walls of the sheath.

In some embodiments, other passages can be integrated into the tubular sheath to allow the steering wires (which can be referred to as cables) to be slidingly coupled to the walls of the tubular sheath, such as hooks or rings that can be formed by the material removed to create the slots that are rigidly affixed to the inner or outer wall of the tubular sheath and shaped to allow metal wires to slide relative to the tubular sheath walls. These passages can be formed inside or outside of the remaining tubular structure of the sheath. In some embodiments, the lumen wall can include a metal spring material that forms a tubular foil that makes up the inner or outer wall of the lumen. A flexible material, such as silicone, nitrile, or latex, can be molded to this foil structure allowing wires to be embedded in the flexible material. The rigid material, having circumferential slits, provides a rigid, but controllably flexible structure to control the movement of the flexible tube created by the molded flexible material. In some embodiments, the tubular sheath can be formed of a two part, concentric structure where grooves in the inner wall of the outer structure and in the outer wall of the inner structure mate, creating a roughly cylindrical, oval, or rectangular channel within which steering wires can be placed.

Suitable materials for the steering wires can include braided or monofilament wires/cables of any desired material, such as stainless steel, memory shape wires (that can be shortened or lengthened via electric current, nichrome, or a variety of plated wires, etc. In some embodiments, wires are semi-rigid, allowing them to be pulled or pushed to deform the deflection of the sheath. In some embodiments, the steering wires are affixed to the distal end of the sheath, while the proximal end is allowed to be selectively moved relative to the proximal end of the sheath.

The steering cables can be driven by any suitable driver. For example, a screw and nut configuration as the proximal end can allow the wire to be used to apply tension or extension pressure to the distal end, depending on how the threads are turned (which can be via a motor). In some embodiments, the wires are configured to move relative to the sheath in a Bowden cable arrangement. In some embodiments, cables can be pulled or driven by gears or pulleys. In some embodiments, electromagnetic linear actuators are coupled between a housing affixed to the proximal ends of the wires and to the proximal ends of individual or groups of wires, allowing selective tension or pressure to be applied under electronic control. In some embodiments, the actuators comprise pneumatic or hydraulic pistons rather than electromagnetic drivers.

In some embodiments, steering wires are rigidly affixed to the sheath at the distal end, while in others, each wire can be looped (e.g., in a U-shape) from one longitudinal passage to an adjacent longitudinal passage, allowing either proximal end of that wire to be pulled, while providing tension (or pressure) to both wire sections, allowing more uniform flexion forces with fewer actuators. A low friction wire/sheath interface at the distal end can facilitate the sliding of the looped wire.

In some embodiments, each steering wire is affixed at at least one proximal end, while the middle of the wire is again looped at the proximal end of the sheath, allowing each wire to pass through four passages in the sheath body. A rotating or sliding pulley apparatus mated to that center, proximal portion of the wire can allow tension or pressure on all four portions of the wire, by moving the pulley structure toward or away from the proximal end of the sheath structure. Similarly, by pulling on one portion of the center, proximal wire section while pressing on the other side (e.g., by rotating sheathes that engage the wire are the proximal end) of that section, two of the wire sections passing through the sheath will experience tension, while the other two experience extension. By arranging the pairs of passages in the sheath for these pairs of sections to be radially opposite, a single actuation of the wire can cause tension on one side of the sheath, while extension pressure is applied to the opposing side of the sheath.

In some embodiments, some of the steering wires only pass partially through the sheath in the longitudinal direction, allowing individually articulable sections, such as a proximal section and a distal section.

Embodiments of the present invention can utilize a linear bearing or linear bushing to mechanically couple the inner rotating shaft of the tool with the inner wall of the lumen of the sheath. By using bearings (linear ball bearings or bushings), the inner shaft can rotate relative to the rotatably rigid outer wall of the lumen, allowing the tooltip to spin. These linear bearings and bushings can also allow the rotating shaft to be shifted relative to the lumen in a distal or proximal (longitudinal) direction. This can allow retraction or extension of the tooltip on demand.

The rotating shaft can be any suitable design that allows torque to be transferred from a motor at the proximal end of the shaft to a surgical burr at the distal end, while allowing the shaft to flex. For example, the rotating shaft can be a metallic filament, plastic filament, etc. In some embodiments, the rotating shaft is a slotted tube of a design similar to the sheath (without steering wires). In some embodiments, the flexible shaft is a coil spring or torque coil, which allows torque transfer and flexibility. A rotary tool can be powered by any electromagnetic motor or pneumatic motor and rotate with suitable torque and RPMs suitable for removing the target tissue. For example, the tool can rotate at a fixed or variable speed of 10,000-60,000 RPMs to remove bone tissue.

The linear bearings between the lumen wall and the outer surface of the flexible rotating shaft can be spaced at regular intervals along the length of the shaft. These bearings can include stainless steel linear ball bearings that are affixed to the inner wall of the lumen or the outer surface of the rotating shaft. Linear bushings can also be used that allow rotation and sliding of the inner shaft. Suitable materials for such a bushing can include any combination of oil-impregnated metal, plastic, PTFE, ultra-high molecular weight plastics, or any other surgical grade surface that has a low coefficient of friction relative to the outer wall of the shaft or the inner wall of the lumen. In some embodiments, a combination of bushings and bearings can be used.

Figure 2A:
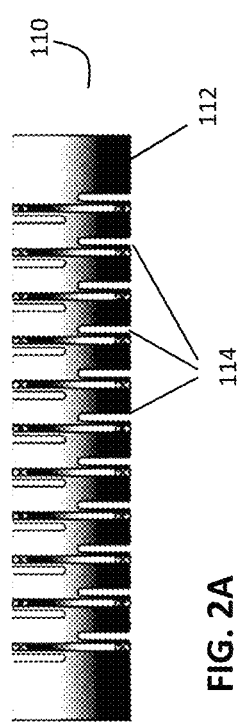
FIG. 2A is a side view of an exemplary tubular sheath for use with some embodiments.
Figure 2B:
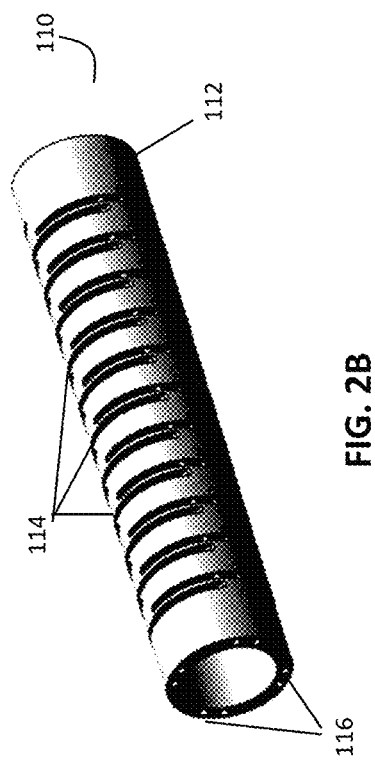
FIG. 2B is a perspective view of an exemplary tubular sheath for use with some embodiments.

Flexion of the lumen can repeatedly direct the position of the tooltip relative to the handpiece that controls the proximal end of the sheath. FIG. 2A shows a side view of an exemplary flexible tubular sheath 110 having a rigid metal body 112 and a repeating series of circumferential slots 114 in an exemplary spring steel material. FIG. 2B is a perspective view of that flexible tubular sheath 110, including steering cable channels 116 within the body 112 of the sheath. These channels 116 may be drilled in walls of the steel in the spring steel, or placed within flexible material housed inside of the outer spring steel wall. These channels 116 allow sliding movement of the steering cables, allowing cables to push or pull to change the proximal/distal length of that portion of the lumen via tension or expansive forces.

Figure 3A:
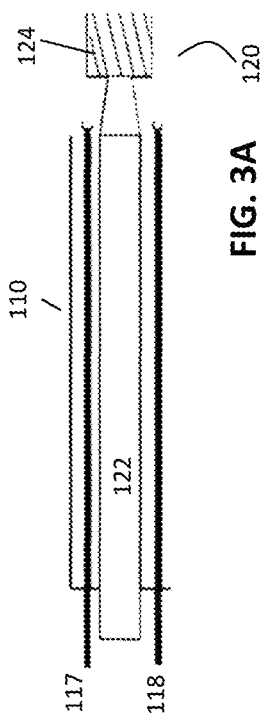
FIG. 3A is a cross-sectional view of an exemplary rotary tool with a flexible shaft and sheath for use with some embodiments in a straight configuration.
Figure 3B:
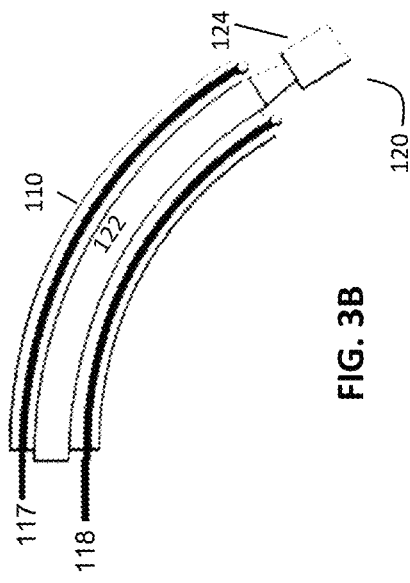
FIG. 3B is a cross-sectional view of an exemplary rotary tool with a flexible shaft and sheath in accordance with some embodiments in a flexed configuration.
Figure 3C:
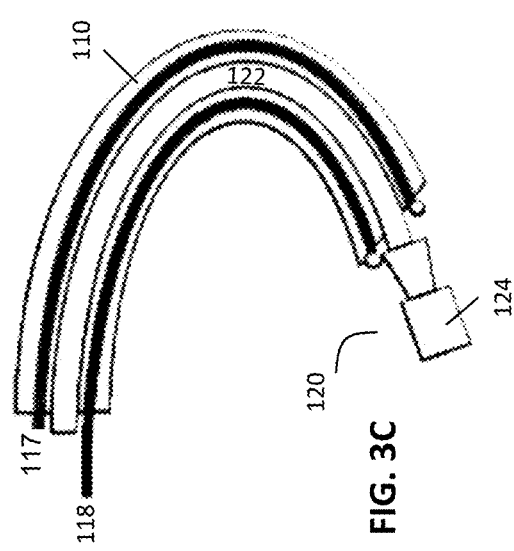
FIG. 3C is a cross-sectional view of an exemplary rotary tool with a flexible shaft and sheath in accordance with some embodiments in a flexed configuration.

FIGS. 3A-3C are cross sectional views that illustrate how steering cables in the channels 116 can control the flexion of the sheath 110. Flexion of the sheath can be controlled by semi-rigid or tensile steering cables 117 and 118. Note that in some embodiments, four or more cables are used, but only two are used to illustrate their operation. By pulling a steering cable, the lumen wall experiences a contraction force along that proximal/distal path defined by that steering cable. By pulling the steering cables on one side of the sheath, the lumen will deform in response to this contractive force, shortening on that side. In some embodiments, semi-rigid steering wires can be used to also provide an expansive force on the other side of the sheath, causing that side of the lumen to extend. By utilizing contractive and expansive forces, one side of the lumen of the sheath can contract while the other side extends. This can result in a high degree of flexion of the sheath and the inner lumen, steering the inner rotating shaft. In some embodiments, greater than 90° of flexion of the lumen is achievable. In some embodiments, up to 180° of the lumen flexion is achievable.

FIG. 3A shows a cross-sectional view of an exemplary sheath 110 that forms a lumen around a rotating shaft 122 of a rotary tool 120, which has a burr 124 at the end. Steering cables 117 and 118 are embedded within the sheath 110. The pose of the sheath 110 in FIG. 3A shows zero degrees of flexion. FIG. 3B shows a cross-sectional view of the exemplary deflection of the sheath 110 and the tooltip 124 by placing tension on the lower steering cable 118, moving the proximal end out of the sheath. It should be appreciated that by placing a series of steering cables/wires circumferentially around the sheath, this deflection can be in any radial direction. Furthermore, because the mechanical properties of the sheath can be well-defined, the tool deflection can be tracked based on a tension force applied or the distance traveled by the proximal end of the steering cable 118. For example, if the steering cable 118 has been pulled in by a certain number of millimeters, the mechanical response of the flexible sheath 110 can be calculated because of the semi-rigid nature of the structure of the sheath.

FIG. 3C shows a cross-sectional view of the exemplary deflection of the sheath 110 and the tool 120 when the sheath is at full flexion according to some embodiments. In this example, tension is applied to the lower steering cable 118, causing the sheath 110 to contract along the side of the cable. Pressure is applied distally to the second semi-rigid steering cable 117, causing the sheath 110 to elongate on the side of the second steering cable. This can result in greater than 90° of flexion of the sheath 110 and the shaft 122.

Figure 4:
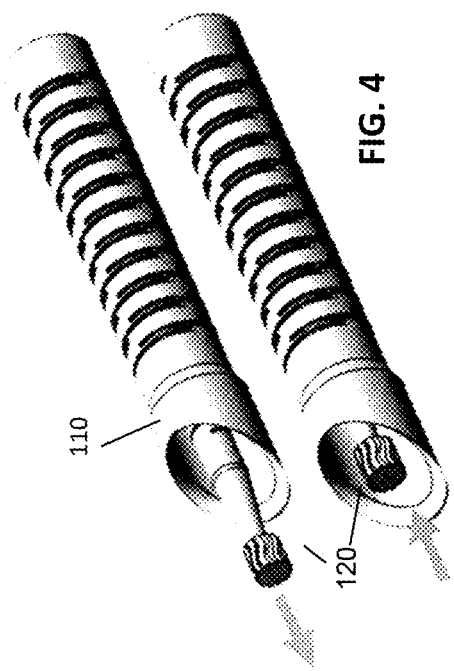
FIG. 4 is a pair of perspective views of an exemplary rotary tool in accordance with some embodiments where the tooltip is extended or retracted.

In some embodiments, the rotary tool 120 can be stopped when the position of the tooltip 124 goes outside (or starts to go outside) of an intended area. This can be accomplished by sending a control signal from a controller to the motor that rotates the shaft 122, causing the motor to halt. In some embodiments, the tooltip 124 can be retracted into the sheath 110 when the tooltip extends beyond an intended area. This can be used along with or instead of halting the motor that spins the shaft 122. The use of linear bushings and linear bearings can allow a controller/processor to send a control signal to a linear actuator (electric, hydraulic, or pneumatic) to retract the tooltip 124 relative to the outer sheath 110 as the tooltip encroaches the boundary of the resection area. This feature is shown in FIG. 4. In the top example, rotary tool 120 is fully extended beyond the distal end of sheath 110. This allows the tooltip 124 to engage tissue when it is rotated. The bottom example of FIG. 4 shows the rotary tool 120 fully retracted, such that the tooltip 124 does not extend beyond the distal end of the sheath 110. This protects tissue from the tooltip 124, effectively disengaging the tool 120.

Retraction of the tooltip 124 can be used as a safety feature, similar to stopping or slowing down the rotation of the shaft 120 when the tooltip has left the resection area designated in the pre-operative plan. Similarly, through active control of the linear actuator, a feedback control loop can be created in software, such that minute changes in the depth of the sheath 110 can be counteracted by minute retraction of the tooltip 124. The motion profile of the tooltip 124 can be more stable than the depth of the sheath 110, which may be rigidly coupled to a handpiece (for a given flexion) and subject to motions of the surgeon's hand. For example, the surgeon's hands may not be as accurate as a robot arm, but by using active dampening of the motion of the tooltip 124 through counter-retraction of the tooltip in response to unexpected depth changes of the distal end of the sheath 110, a processor can smoothly move the tooltip or approximately stabilize the depth of the tooltip. This may be useful especially as a surgeon approaches the boundary of the resection area with the tooltip 124. As the surgeon moves the tool 120 near the boundary of the resection area, active changes in the depth of the tooltip 124 relative to the handpiece via linear actuation can allow the tooltip to accurately travel just at the boundary of the resection area, removing material at that boundary to a smooth surface, without resecting material outside of the resection area. This can allow the surgeon to more accurately implement the pre-operation plan for resecting tumorous material from the bone. In some embodiments, fully retracting the tooltip 124 into the sheath 110 can be an emergency stop procedure to prevent the tool 120 from damaging additional tissue, should the surgeon slip or otherwise go beyond the resection area. In some embodiments, this retracted position is used during all operation of the tool 120 except when the surgeon intentionally activates the tooltip 124. In some embodiments, tool retraction is not simply a binary operation, allowing dynamic control of the distance between the tooltip 124 and the distal end of the sheath 110.

Figure 5A:
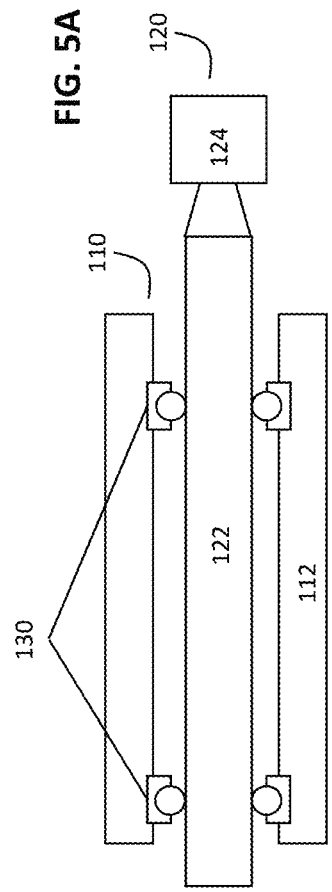
FIG. 5A is a cross-sectional view of an exemplary rotary tool having linear bearings in accordance with some embodiments.

FIG. 5A shows a cross-sectional view of the rotary tool 120 in the sheath 110. It should be appreciated that in all of these examples, the length and thickness of tool components may be exaggerated to illustrate features and do not necessarily reflect a real world example of the ratio of sheath thickness to sheath length. In the example shown in FIG. 5A, linear bearings 130 are spaced at regular distances along the longitudinal length of the sheath 110 and the shaft 122. In this example, only two bearings are shown for illustration purposes, but in some embodiments, more or fewer bearings may be used. Bearings 130 may be linear ball bearings, allowing rotation and longitudinal movement of the shaft 122 relative to the sheath 110. In this example, bearings 130 are registered to the sheath 110 via detents in the wall of the lumen. In some embodiments, bearings 130 may be simply located on a smooth wall of the lumen, roughly held in place by compression and friction. In some embodiments, bearings 130 have outward facing balls, allowing an inner housing of a bearing to be coupled to the shaft 122.

Figure 5B:
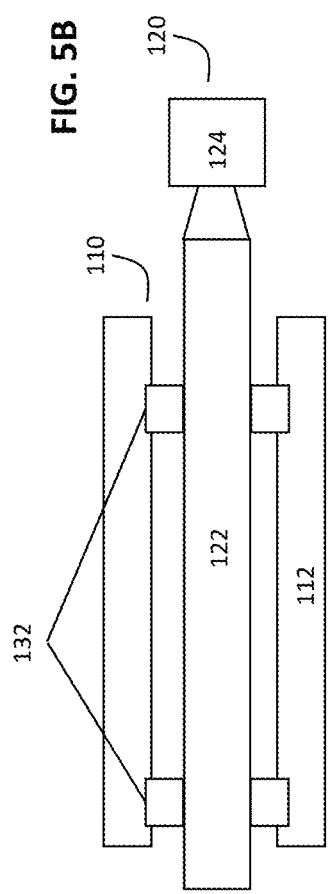
FIG. 5B is a cross-sectional view of an exemplary rotary tool having linear bushings in accordance with some embodiments.

FIG. 5B shows a similar example in which linear bushings 132 are used. Bushings 132 can be a polymer material, an oil-impregnated metallic material, or any other suitable low friction material that provides a low friction interface between the bushings and the shaft 122. In some embodiments, the low friction interface is located between the bushings 132 and the inner wall of the sheath 110. In some embodiments, interfaces are located between the bushings 132 and both the sheath 110 and the shaft 122. In some embodiments, a combination of bearings 130 and bushings 132 may be used, thereby reducing the overall cost or complexity of the tool by allowing bearings to be placed at more critical positions and allowing bushings to provide a supporting role. Like bearings 130, bushings 132 are shown in exemplary detents walls 112 of the sheath 110, but they may also be used without guidance. In such embodiments, the bushings 132 may rely primarily on friction or compression to hold them in place or slots may be used to help grip the bushings. By using bushings 132 or bearings 130, the shaft 122 may rotate and be longitudinally moved relative to the sheath 110.

Tracking of the tooltip 124 relative to the patient's body can be accomplished utilizing conventional surgical navigation techniques. In some embodiments, a handpiece or robotic end effectors that control the position and orientation of the proximal end of the sheath can be optically tracked along with the bone of the patient. Optical tracking can be accomplished by any conventional means available in the art, such as using fiducial marks that are mechanically affixed to a tool and to a patient, such as those used by the NAVIO surgical system. For example, where curettage of a femur or tibia of the patient is being performed, fiducial marks can be mounted on the tibia or femur, allowing optical tracking of the exact position of the patient's bone. Once a handpiece is registered relative to the surface of that bone (such as through a manual registration step by which a registration tool is pressed at predetermined locations on the patient's bone while the tool is optically tracked), fiducial marks on the handpiece can be used to calculate an exact position and orientation of the surgeon's handpiece relative to the surface of the patient's bone. Once registered, all future movement of the handpiece can be used to calculate the exact position of the tooltip 124 relative to the patient's bones. When a flexible tool, such as that shown in FIG. 4, is used, controlling or sensing the position of steering wires within the flexible sheath 110 of that tool can be used to determine a robust approximation of the location of a tooltip 124 through calculations using a model of that tool. The model can include a model of how much the lumen of the flexible sheath 110 deflects for a given change in position of the steering wire, the length of that sheath, the size of the rotary tooltip 124, the length of the shaft 122 of the rotary tool, and a model of the exact orientation of the flexible sheath 110 relative to the fiducial marks on the surgeon's handpiece.

This allows the position of the tooltip to be optically tracked based on fiducial marks of the handpiece/robot end effectors and position sensors that detect the position of the steering cables of the tool. Alternatively, a fiber-optic transducer can be used in some embodiments to sense the angular deflection of the tooltip 124, rather than the position of the steering cables. This allows a direct measurement of the location of the tooltip. By controlling the location of the tooltip 124, or at least by tracking it, robotic control of the tooltip can be achieved. For example, once a surgeon engages the tool and the patient's bone, the robot can turn on the rotary motor that spins the surgical tooltip 124 automatically based on the calculated position of the tooltip.

Optical tracking can be used to determine whether or not the tooltip 124 is near the patient's bone. At the time of engagement, for safety, the tooltip 124 can be deactivated until the surgeon brings the tooltip to the surface of the patient's bone. There, the tooltip 124 can begin boring into the patient's bone. Based on preoperative imaging, a predetermined three-dimensional area of the patient's bone can be identified for resection. A processor within the tool, based on optical tracking and sensing of the flexion of the tool, can determine whether the tooltip 124 is still within that area of resection. While the tooltip 124 is in the area of resection, the motor can be engaged under processor control. This allows the surgeon to resect bone tissue using the tooltip 124 while the tool is in the predetermined resection area.

During the resection process in the resection area, a processor can control the speed of rotation of the tooltip 124. The speed can be constant or variable based on a motion profile that optimizes the tool for cutting of bone material. For example, certain areas may be designated as requiring a faster or slower speed based on the physical model of the bone. Because the sensors tell the processor the position of the tooltip 124 relative to the patient, the processor can also determine where the tooltip is in the resection area. Based on that positioning, the processor can control the speed of the tooltip 124 such that the tooltip stops or substantially slows down if the tooltip leaves the resection area. This can allow the tooltip 124 to safely cut the material within the resection area without unnecessarily removing tissue from the patient's bone that was not designated for resection. Cutting can be coupled with suction or saline flushing to fully debride the resected bone tissue. Based on the position of the tooltip 124, the processor can give the surgeon haptic feedback in the form of rapid changes to the rate of rotation of the tooltip, causing a vibrating or pulsing sensation to be noted by the surgeon holding the tool.

FIG. 6 shows a diagrammatic view of an exemplary surgical tool 140 for use in resecting the bone tissue in accordance with some embodiments. The tool 140 includes a tool body 142 (not shown to scale or to specific shape, but represented diagrammatically). The tool body 142 can be configured to be an ergonomic handle for a handpiece for use by a surgeon or configured to interface with end effectors of a robot arm for robotic surgery. The tool body 142 can include any display or input/buttons that may be useful for operation. The exact position and orientation of the tool body 142 within a surgical scene can be determined optically by the use of physical fiducial marks 144 affixed to the tool 140. The fiducial marks 144 can take on any suitable physical characteristics that can aid in fiducial representation of the location and orientation of the tool body 142. For example, the fiducial marks 144 can include three points that define a plane, where each mark is IR or UV reflective or a different color than other objects in the surgical scene. This can allow a camera (via IR/UV/visible light illumination) to create unique physical marks in the camera's scene that can be interpreted by a processor using geometric imaging algorithms known in the art to create an exact physical model the location and position of the tool body 142. As long as the relationship between the fiducial marks 144 and the tool body 142 is fixed and well-known by the processor, camera tracking of the fiducial marks can, at all times during the surgery, create an accurate approximation of the exact location and position of the tool body and, by extension, the tooltip 124 of the tool 140.

Housed within the tool body 142 is a motor 146. The motor 146 is selected to have suitable speeds and torque to drive the cutting tooltip 124 via a shaft 122 in a manner suitable for removing tissue during surgery. For example, the motor 142 may be a brushless DC motor or a high-speed pneumatic/air-driven motor. The motor 146 is controlled by a controller 148, which includes a processor and suitable hardware for receiving sensor signals and driving the motor. The controller 148 can be enclosed within the tool body 142 or external thereto. The depth of the tooltip 124 relative to the sheath 110 is controlled by a depth controller 150. The depth controller 150 can include a linear actuator that slides the shaft 122 relative to a mechanical coupling mounted to the motor 146. This allows the shaft 122 to slide away from or toward the motor 146, allowing the shaft and the tooltip 124 to move proximately or distally relative to the sheath 110.

The sheath 110 can be rigidly mounted at an intersection with the tool body 142. This enables the controller 148 to accurately model the location of the tooltip 124 based on the observed deflection of the sheath 110 and the depth provided by the depth controller 150. In some embodiments, the depth controller 150 includes optical encoding to accurately determine the longitudinal depth of the shaft 122 relative to the motor 146. In some embodiments, no sensors are needed, and the actuation by the depth controller 150 can be assumed based on input from the controller 148.

A steering controller 152 may be mounted in the tool body 142 adjacent to the proximal portion of the sheath 110. The steering controller 152 includes physical mechanisms that provide tension or extension forces to steering cables in the sheath 110, as explained herein. This can include motors (with belts, chains, or gears to drive screws, sheaves, cams and the like) and/or linear, electromagnetic, or hydraulic/pneumatic actuators. A driving portion of the steering controller 152 can include linear actuators, motor drive gears or pulley sheaves, or any other suitable mechanism to cause tension to or otherwise change the depth of retraction or extension of steering cables within the sheath 110. In some embodiments, the steering controller 152 controls four or more steering cables that operate independently. In some embodiments, the steering controller 152 utilizes a series of screws, and a washer within the steering controller is physically coupled to each steering cable. By adjusting the screws, the depth and angle of each washer can be adjusted, which changes the relative depth and retraction/extension of each of the steering cables and allowing the flexion of the sheath 110 to be reliably controlled.

Both the depth controller 150 and the steering controller 152 may be controlled by the controller 148. In some embodiments, the steering controller 152 in the depth controller 150 includes one or more sensors that determine the relative extension or retraction of the steering cables and the shaft 122. This information is used by the controller 148 to determine a reliable model of the location of the tooltip 124 relative to the tool body 142. The position information determined by the controller 148 can be fed to another processor that is involved in calculating the position and orientation of the tool body 142 based on imagery of the fiducial marks 144 to create an accurate physical model of the position of the tooltip 124 in the surgery scene. By comparing that location to the model of bones in the patient in the surgery scene (not shown), the relative location between the tooltip 124 and the predetermined resection area can be determined. This information can be electronically sent to, or calculated by, the controller 148 to determine how the motor 146, the depth controller 150, and the steering controller 152 should react to the position of the tooltip 124. For example, if the controller 148 determines that the tooltip 124 is leaving the predetermined resection area, the motor 146 can be slowed or stopped, and the depth controller 150 can be sent a command to retract the tooltip 124 within the sheath 110 to prevent cutting the patient's bone beyond the resection area. The controller 148 can control the speed and retraction/extension of the tooltip 124 as described herein. In some embodiments, the controller 148 can also send a command to the steering controller 152 to compensate for an error using the flexion of the sheath 110 to mitigate harm as well.

Also shown is image tracking system 154, which comprises at least one optical camera to track the fiducial marks of the patient and the fiducial marks 144 on the tool body 142. The image tracking system 154 is in electronic communication (such as via a wireless system or hardware system, including any intervening processors) with the controller 148. Processors in the image tracking system 154 can work in conjunction with the controller 148 to determine the location of the tooltip 124 based on the fiducial marks 144. Based on this information, the controller 148 or another processor working with the controller within the system can determine whether or not a cutting tool of the tooltip 124 should be moved, stopped, or otherwise driven at different RPM.

FIG. 7 is a flowchart of an exemplary method for operating an exemplary rotary tool for use in some embodiments. Method 160 includes the steps that will be executed to operate the rotary tool in a surgical environment. At step 162, a preoperative surgical plan is created. This plan could be created through any conventional means including looking at computer simulations and medical imagery to determine the best choice of treatment for a patient. This step can involve significant human input, such as relying on a surgeon's skill to select the best treatment. During this step, the extent of any tissue to be removed can be identified based on imagery and surgical experience.

At step 164, the surgeon initializes the image tracking system in the operating room. This can include any standard procedures for using a robotically enhanced surgical unit that includes image tracking, such as the NAVIO surgical system. Once the image tracking system is initialized, an embodiment of a rotary tool can be selected by the surgeon once the patient's soft tissue is opened up through conventional surgical means. At step 164, the surgeon registers the fiducial marks of the handheld tool with the image tracking system. This can include placing the surgical tool in the field of view of a camera/robotic image tracking system and placing the tip of the tool or a registration device in contact with salient features of a patient's bone that are relevant to the surgical procedure. This informs the image tracking system of the baseline relationship between the patient's bones or other tissues and the fiducial marks on the tool. From there, the image tracking system can track movement of the fiducial marks using one or more cameras to always have a model of where the tool body and tooltip are relative to the patient.

At step 166, a processor associated with the image tracking system determines the location of a preoperatively-planned resection area in the model of the surgical environment. The boundaries of this area can be identified during the preoperative plan at step 162. The boundaries of the resection area during this step are identified relative to the patient's frame of reference. Once in the surgical environment, the image tracking system identifies the boundaries of that resection area in the model of the current space that includes the model of the patient's tissues and a model of the surgical tool.

At step 168, once the surgeon has properly registered the tool with the image tracking system and the image tracking system has a model of the location and orientation of that tool relative to the patient's tissues, the surgeon can begin engaging the patient's tissues with the tool. Engagement of the tool can include turning on the motor that spins the cutting tip of the tool. Once the surgeon engages the tool, the tool can begin cutting into the tissues of the patient, in accordance with the preoperative plan. In some embodiments, the surgeon will rely on his manual skill and experience as a surgeon to perform the procedure. In some embodiments, the surgeon can operate a robotic arm, where the tool is placed in end-effectors of that robot arm. One advantage of using a robot arm is that operation of the tool may be more stable without the natural jitters or dithering in the motion of the hand. Note that some embodiments mitigate this problem via dynamic retraction/extension or flexion of the tool to compensate for erroneous tool motion. One advantage of using a tool with a handpiece designed for a surgeon's hand is that a surgeon can immediately intervene and at all times keep the patient safe via direct human interaction with the tool.

Once the tool has been engaged with the patient's tissue, the surgeon (or robot) can begin moving the tooltip within the patient's tissue. This can include keeping the shape of the tool the same while moving the tool in what the surgeon believes to be the predetermined resection area. Optical tracking of the tool relative to the patient via one or more cameras can verify the surgeon's assumptions. Based on the surgeon's skill or a preoperative plan, at some point during the procedure, it may be desirable to change the shape of the surgical tool by adjusting the flexion of the rotary shaft of the tool. This can be done manually by the surgeon or under processor control. The processor can alter the flexion of the tool in accordance with a preoperative plan or via a routine based on the current location of the tool and a desired outcome.

At step 170, the controller within a surgical tool steers the tooltip by adjusting the steering cables within the sheath of the tool. This can be at the request of the surgeon, an external processor, or based on a routine executed by the controller. In some embodiments, sensors detect the current location and orientation of the tool shaft rather than relying on the expected flexion as determined based on steering input. This can result in more accurate modeling of the location of the tooltip.

At step 172, the controller of the surgical tool controls the speed and depth of the tooltip by changing the speed of the motor of the tool and the longitudinal depth of the tool shaft relative to the tool sheath. This step can be done at any time during operation of the tool and can change on a continuous basis based on a preoperative plan or other routine. By controlling the speed, depth, and the flexion of the tool relative to the tool body, the controller for the tool can adjust the behavior of the tool within the patient's tissue for a given position and orientation. In some embodiments, during normal operation within the resection area, the tool will be fully extended or extended to a nominal position relative to the sheath. At any time, depending on the needs of the surgical plan and the current state of the tool, the tooltip can be extended or retracted by the controller.

At step 174, the processor determines the current position of the tooltip. This determination can be based on a combination of the current flexion of the tool, the current extension of the tooltip, and the optically determined orientation and position of the tool body relative to the patient. In some embodiments, steps 170 through 174 can be performed under processor control in real time, allowing the processor of the tool to compensate for erroneous or non-smooth motion of the tool body, compensating in a controlled manner for small movements by a robot arm or a surgeon's hand. Erroneous tool motion can be monitored in real-time using one or more accelerometers in the tool body in addition to optical tracking. Due to practical limitations of the feedback loop, this compensation may be only a partial compensation for non-ideal movement, but it can mitigate rough movement of the tool to result in smoother operation of the tooltip within the patient's tissue.

At step 176, the controller for the tool compares the current location of the tooltip to the predetermined resection area to determine whether or not the tool is safely within that area. If so, operation continues at step 170, continuously during operation of the tool, adjusting the speed and the depth and determining the current position of the tool.

If the tooltip is determined to be outside the resection area or nearing the boundary of the resection area, the operational state of the tool can be adjusted. For example, in method 160, the controller of the tool is programmed to cease operation of the tool if the tooltip leaves the resection area. In this example, at step 178, once it has been determined that the tooltip is outside of the resection area, the tool can be stopped. This can include stopping the rotation of the tool and retracting the tip inside the sheath to prevent further damage to the patient's tissue. At step 180, the surgeon is alerted either via a display, audio alert, or haptic feedback, such as pulsing the motor.

It should be appreciated that, in some embodiments, steps 178 through 180 can be less binary. For example, as a surgeon moves the tooltip near the boundary of the resection area, the controller of the tool can dynamically retract and extend the tooltip to allow the tooltip to more smoothly touch the boundary of the resection area to ensure full curettage of the resection area. Similarly, the tool may be slowed down as the tool nears the boundary of the resection area. A combination of retraction and altering the speed can result in a safe, accurate curettage of all tissue within the resection area. Similarly, step 180 can occur before there is a need for step 178. For example, the surgeon may be alerted through audible alarms, graphical display, or haptic feedback when the tip nearing the ad of the resection area determined by the preoperative plan. Once the tool has responded to the tool reaching the boundary of the section area, the surgeon can reengage the tool at step 168 once the tool is back within the resection area.

Figure 8:
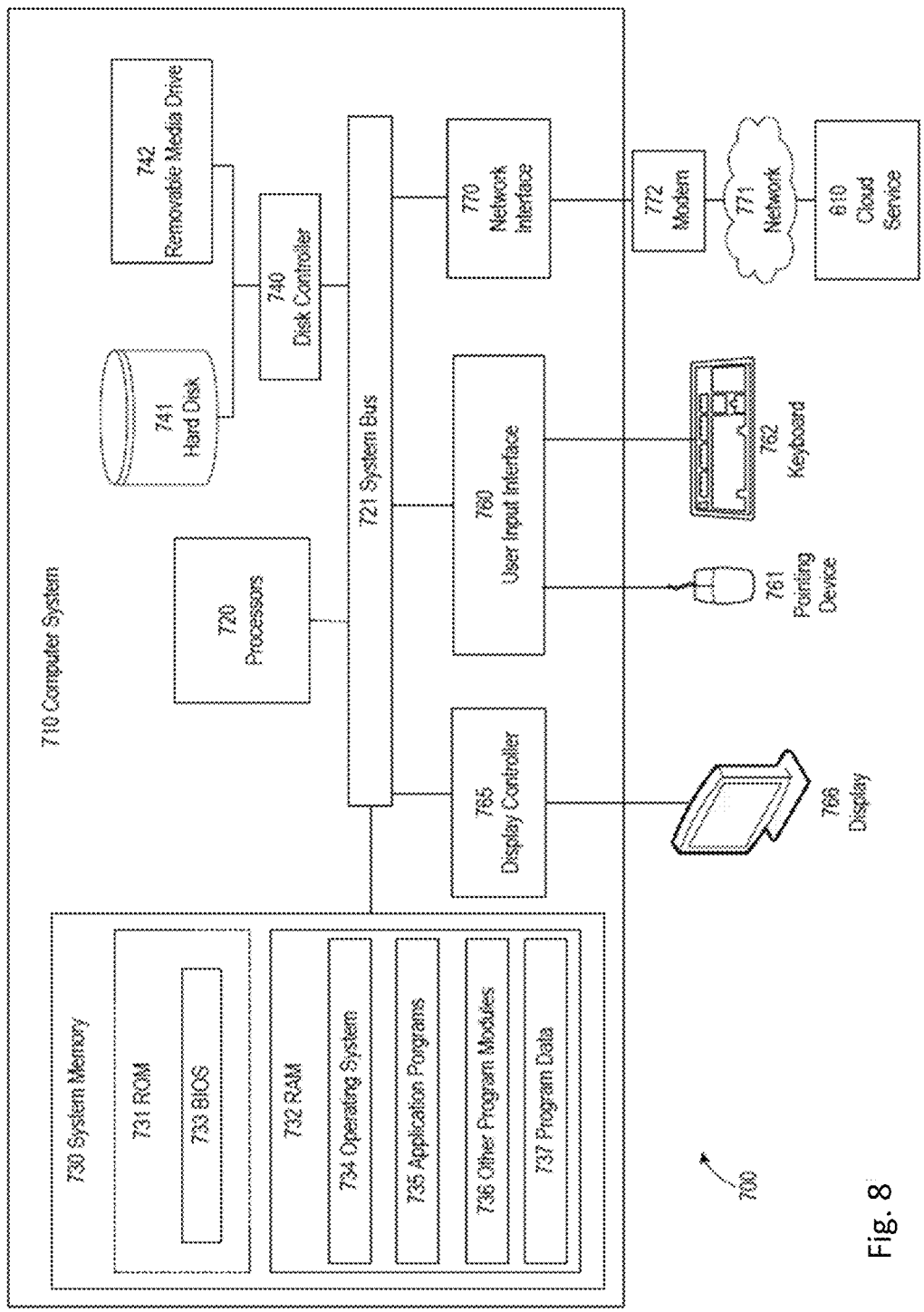
FIG. 8 is a system diagram for an exemplary computing system that may be used with some embodiments.

FIG. 8 shows an exemplary the computer system that can be used with some embodiments. For example, such a computer system could be used to control operation of an exemplary rotary tool, with the image tracking system of the robotic surgery system, or as the controller 148. The controller 148 in FIG. 6 may include a subset of the components described in FIG. 8 coupled with drive and I/O circuitry suitable for controlling the rotary tool. The controller 148, in general, includes at least a processor and memory containing instructions and data and any peripheral electronics suitable for performing the functions described herein. The controller 148 may also be in wireless communication with other computing systems.

Computer system 710 may include a communication mechanism such as a system bus 721 or other communication mechanism for communicating information within the computer system 710. The computer system 710 further includes one or more processors 720 coupled with the system bus 721 for processing the information. The processors 720 may include one or more central processing units (CPUs), graphical processing units (GPUs), or any other processor known in the art.

The computer system 710 also includes a system memory 730 coupled to the bus 721 for storing information and instructions to be executed by processors 720. The system memory 730 may include computer readable storage media in the form of volatile and/or nonvolatile memory, such as read only memory (ROM) 731 and/or random access memory (RAM) 732. The system memory RAM 732 may include other dynamic storage device(s) (e.g., dynamic RAM, static RAM, and synchronous DRAM). The system memory ROM 731 may include other static storage device (s) (e.g., programmable ROM, erasable PROM, and electrically erasable PROM). In addition, the system memory 730 may be used for storing temporary variables or other intermediate information during the execution of instructions by the processors 720. A basic input/output system (BIOS) 733 contains the basic routines that help to transfer information between elements within computer system 710, such as during start-up, may be stored in ROM 731. RAM 732 may contain data and/or program modules that are immediately accessible to and/or presently being operated on by the processors 720. System memory 730 may additionally include, for example, operating system 734, application programs 735, other program modules 736 and program data 737. The application programs 735 may carry out any of the methods or functions described as being performed by processors herein.

The computer system 710 also includes a disk controller 740 coupled to the system bus 721 to control one or more storage devices for storing information and instructions, such as a hard disk 741 and a removable media drive 742 (e.g., compact disc drive, solid state drive, flash memory, etc.). The storage devices may be added to the computer system 710 using an appropriate device interface (e.g., a small computer system interface (SCSI), integrated device electronics, Universal Serial Bus (USB), or SATA).

The computer system 710 may also include a display controller 765 coupled to the bus 721 to control a display 766, such as a liquid crystal display (LCD), for displaying information to a computer user tasked with programming or maintaining the controller computing system of the stationary robot system. The computer system includes an input interface 760 and one or more input devices, such as a keyboard 762 and a pointing device 761, for interacting with a computer user and providing information to the processors 720. The pointing device 761 may be, for example, a mouse or a pointing stick for communicating direction information and command selections to the processors 720 and for controlling cursor movement on the display 766. The display 766 may provide a touch screen interface which allows input to supplement or replace the communication of direction information and command selections by the pointing device 761.

The computer system 710 may perform a portion or all of the processing steps of embodiments of the invention in response to the processors 720 executing one or more sequences of one or more instructions contained in a memory, such as the system memory 730. Such instructions may be read into the system memory 730 from another computer readable medium, such as a hard disk 741 or a removable media drive 742. The hard disk 741 may contain one or more datastores and data files used by embodiments of the present invention. Datastore contents and data files may be encrypted to improve security. The processors 720 may also be employed in a multi-processing arrangement to execute the one or more sequences of instructions contained in system memory 730. In alternative embodiments, hard-wired circuitry may be used in place of or in combination with software instructions. Thus, embodiments are not limited to any specific combination of hardware circuitry and software.

As stated above, the computer system 710 may include at least one computer readable medium or memory for holding instructions programmed according to embodiments of the invention and for containing data structures, tables, records, or other data described herein. The term "computer readable medium" as used herein refers to any medium that participates in providing instructions to the processor 720 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 741 or removable media drive 742. Non-limiting examples of volatile media include dynamic memory, such as system memory 730. Non-limiting examples of transmission media include coaxial cables, copper wire, and fiber optics, including the wires that make up the bus 721. Transmission media may also take the form of acoustic or light waves, such as those generated during radio wave and infrared data communications.

When used in a networking environment, computer system 710 may include modem 772 for establishing communications over a network 771 with the cloud service 610. Modem 772 may be connected to bus 721 via user network interface 770, or via another appropriate mechanism. Network 771 may be any network or system generally known in the art, including the Internet, an intranet, a local area network (LAN), a wide area network (WAN), a metropolitan area network (MAN), a direct connection or series of connections, a cellular telephone network, WiFi or any other network or medium capable of facilitating communication between computer system 710 and other computers (e.g., robot controller 780). The network 771 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 771.

The embodiments of the present invention may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Unless stated otherwise as apparent from the following discussion, it will be appreciated that terms such as "applying," "generating," "identifying," "determining," "processing," "computing," "selecting," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention. An executable application, as used herein, comprises code or machine readable instructions for conditioning the processor to implement predetermined functions, such as those of an operating system, a context data acquisition system or other information processing system, for example, in response to user command or input.

The functions and process steps herein may be performed automatically or wholly or partially in response to user command. An activity (including a step) performed automatically is performed in response to one or more executable instructions or device operation without user direct initiation of the activity.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure that are within known or customary practice in the art to which these teachings pertain. No claim element herein is to be construed under the provisions of 35 U.S.C. 112(f) unless the element is expressly recited using the phrase "means for.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 components refers to groups having 1, 2, or 3 components. Similarly, a group having 1-5 components refers to groups having 1, 2, 3, 4, or 5 components, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A system for surgically removing tissue of a patient, comprising:
    a tool body containing a motor;
    a flexible rotating shaft drivingly coupled to the motor;
    a flexible tubular sheath located around the flexible rotating shaft, mechanically coupled to the tool body;
    a plurality of bearings placed along a lumen of the flexible sheath, providing support to the flexible rotating shaft, the plurality of bearings being configured to allow the shaft to rotate and to move longitudinally relative to the sheath;
    a plurality of steering wires coupled to the flexible tubular sheath, configured to control the flexion of the flexible tubular sheath;
    a cutting tool at a distal end of the flexible rotating shaft; and
    a controller configured to determine a location of the cutting tool relative to patient tissue and to control the speed of the motor and the longitudinal extension of the flexible rotating shaft in response to the location.

2. The system of claim 1, wherein the flexible tubular sheath includes a plurality of slots through a wall of the sheath.

3. The system of claim 1, wherein the controller is configured to determine whether the cutting tool remains inside a predetermined resection area in the patient tissue.

4. The system of claim 3, wherein the controller is configured to retract the cutting tool within the flexible tubular sheath if the cutting tip is determined to be outside of the predetermined resection area.

5. The system of claim 3, wherein the controller is configured to control the flexion of the flexible tubular sheath and the longitudinal extension of the flexible rotating shaft based on the position of the tool body to remove substantially all of the patient tissue within the predetermined resection area.

6. The system of claim 1, wherein the controller is configured to control the longitudinal depth of the cutting tool relative to the flexible tubular sheath to compensate for motion of the tool body.

7. The system of claim 1, further comprising a camera tracking system that assists the controller in determining the location of the cutting tool, based on the position and orientation of fiducial marks coupled to the tool body.

8. The system of claim 1, wherein the plurality of bearings comprise a plurality of bushings.

9. The system of claim 1, wherein the tool body is configured to be held by a surgeon.

10. The system of claim 1, wherein the tool body is configured to be held by robotic end effectors.

11. A system for surgically removing tissue of a patient, comprising:
    an optical tracking system comprising at least one camera;
    a tool comprising,
        a tool body having fiducial marks to facilitate position and orientation capture by the optical tracking system and containing a motor,
        a flexible rotating shaft drivingly coupled to the motor,
        a flexible tubular sheath located around the flexible rotating shaft, mechanically coupled at a proximal end to the tool body,
        a plurality of bearings placed along a lumen of the flexible sheath, providing support to the flexible rotating shaft, the plurality of bearings being configured to allow the shaft to rotate and to move longitudinally relative to the sheath,
        a plurality of steering wires coupled to the flexible tubular sheath, configured to control the flexion of the flexible tubular sheath and operatively coupled to a driver to provide at least one of tension and extension forces to the plurality of steering wires, and
        a cutting tool at a distal end of the flexible rotating shaft; and
    a controller configured to determine a location of the cutting tool relative to patient tissue and to control the speed of the motor and the longitudinal extension of the flexible rotating shaft within the flexible tubular sheath in response to the determined location.

12. The system of claim 11, wherein the controller is configured to determine whether the cutting tool remains inside a predetermined resection area in the patient tissue.

13. The system of claim 12, wherein the controller is configured to retract the cutting tool within the flexible tubular sheath if the cutting tip is determined to be outside of the predetermined resection area.

14. The system of claim 12, wherein the controller is configured to control the flexion of the flexible tubular sheath and the longitudinal extension of the flexible rotating shaft based on the position and orientation of the tool body to remove substantially all of the patient tissue within the predetermined resection area.

15. The system of claim 11, wherein the plurality of bearings comprise a plurality of bushings.

16. A method for surgically removing tissue of a patient, comprising steps of:
    engaging patient tissue with a rotary cutting tool having a cutting tip on the distal end of a flexible rotating shaft supported in a flexible tubular sheath and a tool body at the proximal end of the sheath having a motor coupled to the shaft;
    tracking the position and orientation of the tool body relative to the patient;
    controlling the flexion of the flexible tubular sheath with one or more steering wires;
    determining a location of the cutting tip relative to a predetermined resection area in the patient tissue; and
    adjusting the flexion of the flexible tubular sheath and a longitudinal extension of the flexible rotating shaft in the sheath, under processor control, to remove patient tissue within the predetermined resection area.

17. The method of claim 16, wherein the adjusting further comprises adjusting the extension to compensate for motion of the tool body.

18. The method of claim 16, further comprising halting the motor and retracting the cutting tip within the flexible tubular sheath if the cutting tip exceeds the predetermined resection area.

19. The method of claim 16, wherein the tracking comprises optically tracking fiducial marks on the tool body relative to fiducial marks on the patient.

* * * * *

UNITED STATES PATENT AND TRADEMARK OFFICE
CERTIFICATE OF CORRECTION

| | | |
|---|---|---|
| PATENT NO. | : 11,471,169 B1 | Page 1 of 1 |
| APPLICATION NO. | : 16/733910 | |
| DATED | : October 18, 2022 | |
| INVENTOR(S) | : Nikou et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 468 days.

Signed and Sealed this
Eleventh Day of February, 2025

Coke Morgan Stewart
*Acting Director of the United States Patent and Trademark Office*